US009182268B2

(12) United States Patent
Blanco-Gomez et al.

(10) Patent No.: US 9,182,268 B2
(45) Date of Patent: Nov. 10, 2015

(54) DEVICE FOR MASS DETECTION OF PARTICLES IN A FLUID MEDIUM, AND IMPLEMENTATION METHOD

(71) Applicant: COMMISSARIAT A L'ENERGIE ATOMIQUE ET AUX ENERGIES ALTERNATIVES, Paris (FR)

(72) Inventors: Gerald Blanco-Gomez, Bouge Chambalud (FR); Vincent Agache, Saint-Martin le Vinoux (FR)

(73) Assignee: Comissariat a l'energie atomique et aux energies alternatives, Paris (FR)

( * ) Notice: Subject to any disclaimer, the term of this patent is extended or adjusted under 35 U.S.C. 154(b) by 311 days.

(21) Appl. No.: 13/628,908

(22) Filed: Sep. 27, 2012

(65) Prior Publication Data

US 2013/0074586 A1    Mar. 28, 2013

(30) Foreign Application Priority Data

Sep. 28, 2011  (FR) ...................................... 11 58681

(51) Int. Cl.
| G01N 15/02 | (2006.01) |
| G01G 3/16 | (2006.01) |
| G01N 15/14 | (2006.01) |
| G01N 5/02 | (2006.01) |
| G01N 15/10 | (2006.01) |

(52) U.S. Cl.
CPC .. *G01G 3/16* (2013.01); *G01N 5/02* (2013.01); *G01N 15/02* (2013.01); *G01N 15/1484* (2013.01); *G01N 2015/1043* (2013.01)

(58) Field of Classification Search
CPC .................. G01N 15/1056; G01N 2015/0288; G01N 2015/1043
See application file for complete search history.

(56) References Cited

U.S. PATENT DOCUMENTS

| 4,897,541 A * | 1/1990 | Phillips ..................... 250/227.21 |
| 6,470,744 B1 * | 10/2002 | Usui et al. ................... 73/290 R |
| 7,157,274 B2 * | 1/2007 | Bohm et al. .................. 435/325 |
| 7,735,358 B2 * | 6/2010 | Bauza et al. .................... 73/105 |
| 7,918,244 B2 * | 4/2011 | Prakash et al. ................ 137/806 |

(Continued)

FOREIGN PATENT DOCUMENTS

| FR | 2 931 549 | 11/2009 |
| JP | 2005156191 A * | 6/2005 |

(Continued)

OTHER PUBLICATIONS

Tan et al., "A trap-and-release integrated microfluidic system for dynamic microarray applications", Jan. 23, 2007, PNAS, vol. 104, No. 4, p. 1146-1151.*

(Continued)

*Primary Examiner* — Laura Martin
*Assistant Examiner* — Herbert K Roberts
(74) *Attorney, Agent, or Firm* — Oblon, McClelland, Maier & Neustadt, L.L.P.

(57) ABSTRACT

The invention relates to a device for mass detection of particles in a fluid medium, including an electromechanical oscillator (7), excitation means (9) fitted so as to cause the said oscillator to vibrate, a fluid supply circuit (5), and a fluid system (11) incorporated in the said oscillator, where the said fluid system (11) is in fluid communication with the fluid supply circuit (5), where the said fluid system (11) includes at least one trapping site (21) configured to trap a particle of interest according to the size of the said particle of interest.

14 Claims, 5 Drawing Sheets

(56) References Cited

U.S. PATENT DOCUMENTS

| | | | |
|---|---|---|---|
| 2004/0072278 A1* | 4/2004 | Chou et al. | 435/29 |
| 2004/0229349 A1* | 11/2004 | Daridon | 435/305.2 |
| 2006/0037915 A1* | 2/2006 | Strand et al. | 210/748 |
| 2008/0230389 A1* | 9/2008 | Ha et al. | 204/451 |
| 2009/0283474 A1* | 11/2009 | Achard et al. | 210/643 |
| 2010/0154535 A1* | 6/2010 | Manalis et al. | 73/32 R |
| 2010/0288689 A1* | 11/2010 | Zhu et al. | 210/336 |
| 2011/0028351 A1* | 2/2011 | Perroud et al. | 506/32 |
| 2013/0112559 A1 | 5/2013 | Renaudot et al. | |

FOREIGN PATENT DOCUMENTS

| | | | | |
|---|---|---|---|---|
| WO | WO-2009/131722 A2 * | 10/2009 | | G01N 1/28 |
| WO | WO 2009/141516 A1 | 11/2009 | | |

OTHER PUBLICATIONS

Ward et. al, "In Situ Interfacial Mass Detection with Piezoelectric Transducers", Aug. 31, 1990, Science Magazine, vol. 249, p. 1000-1007.*

Tanyeri, Melikhan, Eric M. Johnson-Chavarria, and Charles M. Schroeder. "Hydrodynamic trap for single particles and cells." Applied physics letters 96.22 (2010): 224101.*

Lieu, Valerie H. Design, Analysis, and Translation of 3D Hydrodynamic Tweezer Microeddies. Diss. 2013.*

Tan, Wei-Heong, and Shoji Takeuchi. "Dynamic microarray system with gentle retrieval mechanism for cell-encapsulating hydrogel beads." Lab on a Chip 8.2 (2008): 259-266.*

Deng, B., et al. "Parameter Screening in Microfluidics Based Hydrodynamic Single-Cell Trapping." The Scientific World Journal 2014.*

Tan, Wei-Heong, and Shoji Takeuchi. "A trap-and-release integrated microfluidic system for dynamic microarray applications." Proceedings of the National Academy of Sciences 104.4 (2007): 1146-1151.*

Hu et al., "A pi-Shaped Ultrasonic Tweezers Concept for Manipulation of Small Particles", Nov. 2004, IEEE Transactions on Ultrasonics, Ferroelectrics, and Frequency Control, vol. 51, No. 11, p. 1499-1507.*

Search Report issued Oct. 15, 2012 in European Application No. 12 18 6095 (With English Translation of Category of Cited Documents).

Jungchul Lee, et al., "Toward Attogram Mass Measurements in Solution with Suspended Nanochannel Resonators", Nano Letters, vol. 10, 2010, pp. 2537-2542.

Wei-Heong Tan, et al., "A trap-and-release integrated microfluidic system for dynamic microarray applications", PNAS, vol. 104, No. 4, 2007, pp. 1146-1151.

* cited by examiner

DEVICE FOR MASS DETECTION OF PARTICLES IN A FLUID MEDIUM, AND IMPLEMENTATION METHOD

TECHNICAL FIELD

The present invention concerns the field of mass or gravimetric detection from liquid samples using resonant structures of NEMS/MEMS (Nano/Micro Electro Mechanical System) types.

STATE OF THE PRIOR ART

In many industrial fields the detection of particles in a fluid medium is sought.

This is the case, notably, in the biotechnology field (for example cytometry), where there is a requirement to detect pathogenic agents directly. It is also the case in the field of physical or chemical analysis of fluids for characterisation of micro/nanoparticles.

The mass detection technique is based on the detection and quantification of resonant frequency shifts of an electromechanical oscillator when a particle is deposited on its surface. Throughout the description a particle is understood to mean a bead (whether or not pre-functionalised) of micrometric or nanometric size, but also a chemical or biological object of the protein, peptide, DNA fragment, bacteria, virus or other cells type, etc.

Several works in existence describe the vibration of a resonator or oscillator immersed in a liquid medium. However, the quality factor of such a structure is relatively low, due to the increased dampening of the vibratory motion relating to the high viscosity and density of the liquid medium, compared to a dry medium.

To overcome this problem, work has been undertaken which consists in hollowing out the oscillator in order to confine the solution requiring analysis within the oscillator itself. The article by J. Lee et al may be cited, "Toward Attogram Mass Measurements in Solution with Suspended Nanochannel Resonators", Nano letters, 2010, 10, 2537-2542. The oscillator takes the form of a cantilever beam which contains a fluid stream. The oscillator is made to vibrate by electrostatic coupling, whilst the fluid requiring analysis flows within the fluid stream, and is controlled by a pressure differential. This device enables biological species to be detected in a liquid medium, whilst maintaining the oscillatory motion in a dry environment (air or in a moderate vacuum). There are two mechanisms to keep particles at the free end of the beam temporarily. A first mechanism suitable for out-of-plane vibrating structures concerns the adjustment of the centrifugal force caused by the vibratory motion of the oscillator, where the flow is controlled by a pressure differential in the fluid stream. A second mechanism for temporarily maintaining particles concerns a rapid alternation of the fluid's direction of flow.

However, these types of mechanism can lead to particle release, and in addition the system is blocking: as soon as a first particle is attached the particles conveyed from an upstream tank will thus also be attached after the first particle. In addition, the user must have equipment which is capable of controlling the flows of pressurised liquid. Furthermore, the detection of the mechanical resonance is accomplished by an optical assembly consisting of a laser, a photodiode and a signal-processing electrical circuit, which add to the system's overall encumbrance.

Other works have proposed oscillators including a fluid stream the inner wall of which is functionalised in order to enable biological or chemical species, determined according to their affinity, to be bonded. This presupposes a prior and inconvenient step of chemical functionalisation throughout the fluid system. In addition, a single device can be dedicated only to the capture of a single biological or chemical species.

International application WO2009/141516 will also be cited, which describes a device for gravimetric detection of particles in a liquid medium guaranteeing a high quality factor, and reduced encumbrance. This device includes a flat electromechanical oscillator including a fluid channel in communication with a through cavity made in the oscillator, and means to actuate the oscillator by electrostatic coupling. The particles are trapped by chemical means by functionalising the inner wall of the cavity within the oscillator, or by electrical means based on a dielectrophoretic effect according to a quadrupole configuration of the electrodes. This device allows particles to be trapped only according to their biological nature.

The object of the present invention is thus to rectify the abovementioned disadvantages by proposing a device for mass detection of particles in a fluid medium of optimal sensitivity, whilst allowing simple, efficient and more distinctive trapping of the particles.

DESCRIPTION OF THE INVENTION

The object of the invention is a device for mass detection of particles in a liquid medium, including an electromechanical oscillator, excitation means fitted so as to cause the said oscillator to vibrate, a fluid supply circuit, and a fluid system incorporated in the said oscillator, where the said fluid system is in fluid communication with the fluid supply circuit, where the fluid system includes at least one trapping site configured to trap a particle of interest according to the size of the said particle of interest.

By choosing the dimensions of the incorporated fluid system in the said oscillator, the particles of interest can thus be detected selectively according to their size.

Advantageously, the said trapping site is located in an antinode of the electromechanical oscillator.

The trapping sites are thus placed in the locations most favourable to optimise detection sensitivity. Indeed, the position of the trapped particle in a position having maximum vibration amplitude increases the resonant frequency, and consequently optimises the detection of the particle and increases the sensitivity of the detection device.

Advantageously, the said trapping site is formed in a fluid trapping branch installed in parallel with a bypass fluid branch, where the said trapping branch has, if the trapping site is free, a lesser fluid resistance than that of the said bypass branch.

More particularly, the fluid system includes a fluid trapping branch forming the said trapping site, and a fluid bypass branch which is installed in parallel with the said fluid trapping branch, where the said fluid trapping branch includes a recess extended by a restriction, where the said fluid trapping and bypass branches are dimensioned such that, when the said recess is free, the said trapping branch has a lesser fluid resistance than that of the said bypass branch, causing a first particle of interest to pass through the trapping branch and to become trapped in the said recess, and when the said recess is occupied, the said trapping branch has a fluid resistance greater than that of the said bypass branch, causing a following particle of interest to pass through the bypass branch.

This enables a purely fluid trapping of the particle to be facilitated, in contrast to more complex trapping mechanisms of the mechanical, optical or electrical types of the prior art.

The present invention thus allows efficient coupling between the positions corresponding to the optimal mechanical mass detection responses of the particles and a passive fluid trapping based on selection by size of the particles.

Advantageously, the fluid system includes multiple trapping sites located in the different antinodes of the said oscillator.

This enables multiple particles to be trapped, which can increase detection efficiency.

The said fluid system is a fluid microsystem or nano system.

According to a particular embodiment of the invention, the trapping sites are arranged in series at the terminals of the supply circuit.

This facilitates trapping of particles sequentially along a fluid path of the said system.

According to another particular embodiment of the invention, the trapping sites are arranged in parallel at the terminals of the supply circuit.

This allows almost-simultaneous trapping of the particles.

According to one aspect of the present invention, the said oscillator is of the hollow cavity plate type, having a shape which may be chosen from among a disk, a ring or a polygon.

According to another aspect of the present invention, the said oscillator is a resonator of the cantilever beam, fixed-fixed beam, nanowire or membrane type.

This enables the oscillator and number of trapping sites to be chosen which are most suitable for the types of particles of interest.

Advantageously, the said oscillator is square in shape, and is of a width and a thickness such that the ratio of the width to the thickness is greater than 10, and for example between 10 and 30.

This is a shape which is easy to manufacture, and which has four trapping sites.

This increases the choice of resonant frequencies and of shape of the fluid system in accordance with the sought application.

Advantageously, the device includes excitation means and detection means which are chosen from among the following means: capacitive, piezo-electrical, piezo-metallic, electro-magnetic, piezo-resistive, thermal, thermo-elastic, and optical.

Advantageously, the supply circuit includes first and second supply channels which are separated from one another by the fluid system, where the said fluid system is in communication firstly with the first supply channel and secondly with the second supply channel, such that the flow rate in the fluid system may be controlled by adjusting the flow rates in the first and second supply channels. It is thus possible to adjust the flow rate finely and simply in the fluid system by defining the differences of the flow rates in the supply channels. This also enables the solutions of interest to be renewed more easily, simply by emptying the supply channels, which have large sections, instead of draining the solutions of interest through the incorporated fluid system, which is of smaller hydraulic diameter.

Advantageously, the detection system includes an assembly of electromechanical oscillators of different scales, where each of the oscillators incorporates a fluid system of a corresponding scale, and where the different fluid systems are in communication with the first and second supply channels.

This enables particles of variable sizes present in the solution of interest to be trapped selectively.

The invention also covers a method for mass detection of particles in a liquid medium, implemented with a detection device according to any one of the previous characteristics, including the following steps:
supplying the fluid system(s) with a solution of interest, such that target particles are trapped in the oscillator,
causing the oscillator(s) to vibrate at (a) resonant frequency(ies), and
detecting a shift of the resonant frequency relative to a reference frequency.

Other advantages and characteristics of the invention will appear in the non-restrictive detailed disclosure below.

BRIEF DESCRIPTION OF THE ILLUSTRATIONS

Embodiments of the invention will now be described, as non-restrictive examples, with reference to the appended illustrations, in which.

DETAILED ACCOUNT OF A PREFERRED EMBODIMENT

Figure 1:
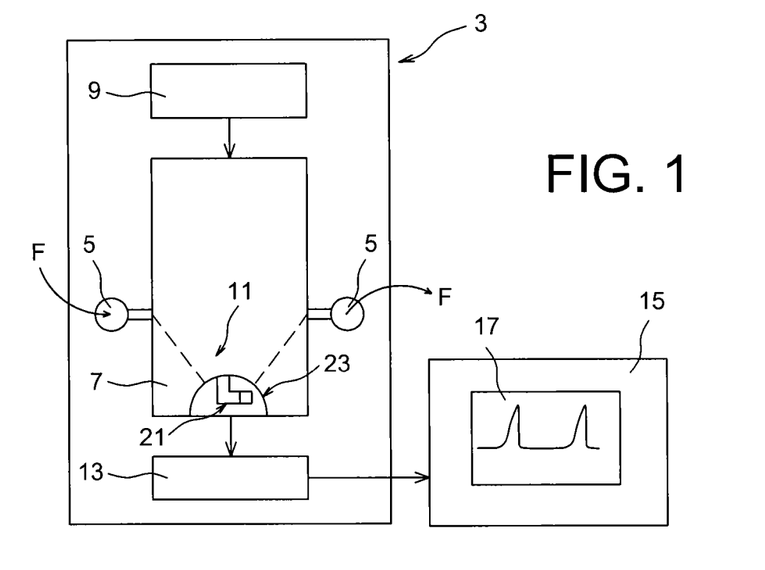
FIG. 1 illustrates very schematically a device for mass detection of particles in a liquid medium, according to the invention.

FIG. 1 illustrates very schematically a device for mass detection of particles in a liquid medium, according to the invention.

Detection device 3 includes a fluid supply circuit 5, an electromechanical oscillator 7 (or resonator), excitation means 9 fitted so as to cause oscillator 7 to vibrate, and a fluid system 11 incorporated in oscillator 7, and supplied with liquid (solution of interest) F by fluid supply circuit 5.

Figure 3:
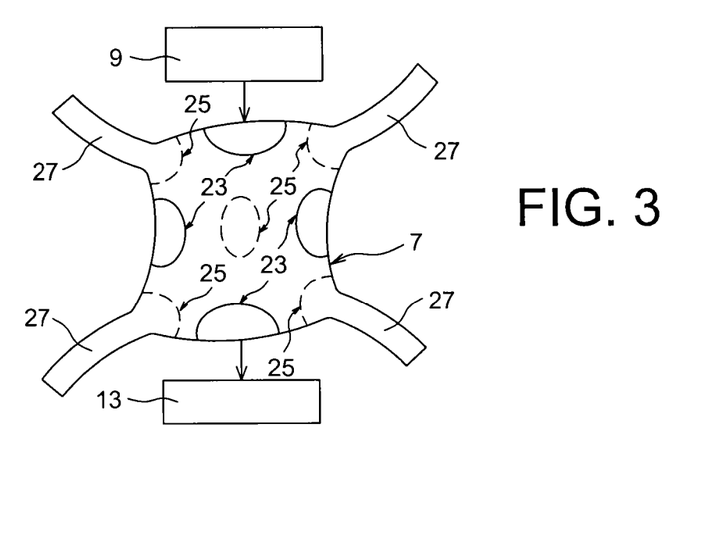
FIG. 3 illustrates a map of the vibration amplitudes for an electromechanical oscillator having the shape of a square plate.

Electromechanical oscillator 7 can have the form of a beam, of wire, a membrane or a plate supported by support means (see FIG. 3). Fluid system 11 is, preferably, incorporated in oscillator 7 such that liquid (or fluid) F analysed by detection device 3 is isolated in a sealed fashion from the environment in which oscillator 7 is actuated. Fluid system 11 is a fluid microsystem or a nanosystem which may consist of channels of roughly parallelepipedic shape etched within oscillator 7.

Excitation means 9 advantageously include electrodes positioned opposite oscillator 7. These electrodes are made and fitted in relation to oscillator 7 such that the latter is able to start to vibrate with a determined vibration mode.

Similarly, detection means 13 to detect the vibration of oscillator 7 can also include electrodes positioned opposite oscillator 7. In this case detection means 13 are advantageously incorporated in detection device 3. These detection means 13 are configured to detect variations of the vibration frequency or resonant frequency of oscillator 7, bearing in mind that every variation of frequency is indicative of a variation of mass of oscillator 7, notably, following a deposition of particles in it. Detection means 13 can be connected to a processing device 15 of the computer type including display means 17 to analyse changes in the resonant frequency, and thus detect particles.

The particles can be functionalised beads, for example metal beads having functionalised surfaces, so as to constitute a surface for collection (or surface for capture) of a chemical or biological species, called the target species. With an oscillator 7 of the same type, it is thus possible to adapt the type of bead introduced, and in particular according to the functionalisation of its outer surface, so as to collect a given chemical or biological species. As the capture proceeds, the mass of oscillator 7 increases, causing a variation of the resonant frequency, determination of which enables the mass of the collected target species to be quantified. This enables the quantity or concentration of the target species in the liquid flowing in fluid system 11 to be estimated. The particles can also be biological species of the cell, bacteria or virus type. The change of the mass of oscillator 7 then enables the action of the species in the oscillator to be determined. For example, a cell can be introduced and subjected to a form of stress (by subjecting it to a particular fluid), and a check can be made as to whether it lives (its mass remains constant, or increases), or whether it dies (its mass diminishes).

It will be noted that detection device 3 can be produced in two portions using a known method described in international application WO2009/141516 of the applicant. A first portion can be structured on a first substrate, and a second portion can be produced on a second substrate bonded on the first substrate. The substrates can be chosen from among materials of a metal, polycrystalline or monocrystalline nature.

In accordance with the invention, fluid system 11 includes at least one trapping site 21 configured to trap a particle of interest according to the size of the particle of interest of the pre-functionalised cells or beads types.

Figure 2:
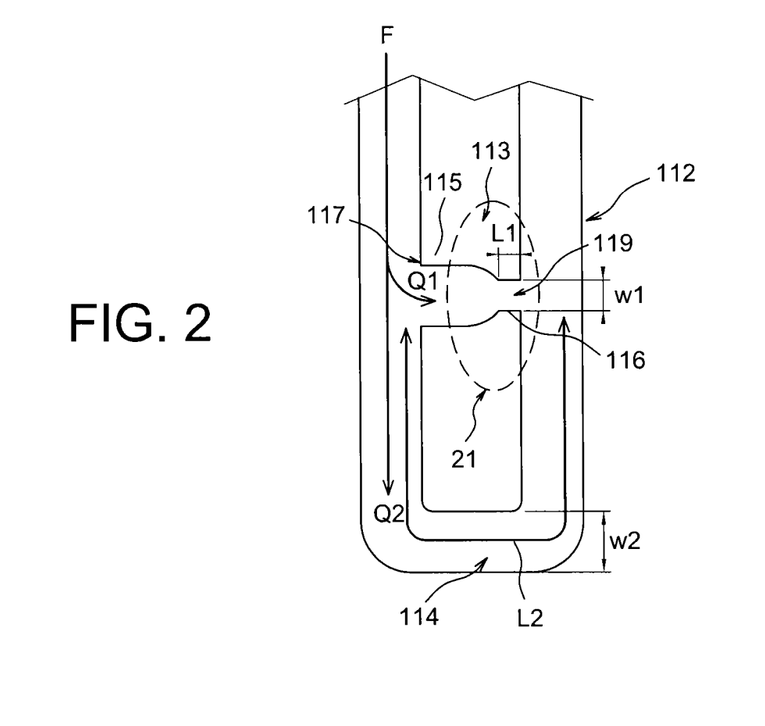
FIG. 2 illustrates a trapping mechanism in the fluid system incorporated in an electromechanical oscillator, according to the invention.

FIG. 2 illustrates the trapping mechanism in the fluid system incorporated in an electromechanical oscillator.

Fluid trapping of a particle of interest is accomplished by a fluid trapping circuit 112 belonging to fluid system 11. This fluid circuit 112 includes a fluid trapping branch 113 installed in parallel with a fluid bypass branch 114, where trapping site 21 is formed in fluid trapping branch 113. Indeed, trapping branch 113 is a channel including a recess 115 (for example of roughly semicircular section), extended by a restriction 116 having a configuration of the funnel type. Recess 115, which is the trapping position, is located upstream from restriction 116 relative to the flow of liquid F.

In trapping circuit 112, the flow of liquid F is thus divided at aperture 117, upstream from recess 115, into two paths which come back together at output aperture 119 of restriction 116. The first path is created by restriction 116 of trapping branch 113 and the second, longer path is formed by bypass branch 114.

Trapping circuit 112 is configured and dimensioned in accordance with the detection applications and the characteristics of the sought particles. The geometry of trapping site 21 is therefore dimensioned selectively according to the size or diameter of the particle of interest. In particular, recess 115 and the aperture between the latter and restriction 116 can easily be dimensioned to accommodate and retain the particle of interest.

The principle of fluid trapping of particles is described in the publication of W. H. Tan et al., "A trap-and-release integrated microfluidic system for dynamic microarray applications", *Proceedings of the National Academy of Sciences of the United States of America*, 2007, 104, 1146-1151. This principle is based on varying the fluid resistance "experienced" by each particle flowing in the fluid system.

Trapping branch 113 and bypass branch 114 are thus dimensionally configured, if trapping site 21 is free, to have a lesser fluid resistance than that of bypass branch 114.

More particularly, when trapping site 21 is free, a given particle tends to pass through trapping branch 113, which has a relatively lower fluid resistance than that of bypass branch 114, and is therefore trapped by trapping site 21. The particle placed in trapping site 21 then acts as an obstacle, thus substantially increasing the fluid resistance of trapping branch 113. The next particle which will "experience" occupied site 21 will thus be subject to very great fluid resistance, and will therefore use bypass branch 114.

This trapping criterion requires that flow rate $Q_1$ in free trapping branch 113 is greater than that $Q_2$ of bypass branch 114 according to the following expression:

$$P = \left(\frac{C_2}{C_1}\right)\left(\frac{L_2}{L_1}\right)\left(\frac{W_2+H}{W_1+H}\right)^2\left(\frac{W_1}{W_2}\right)^3 = \frac{Q_1}{Q_2} \geq 1 \quad (1)$$

where H represents the heights of branches 113 and 114, bearing in mind that all the channels incorporated in oscillator 7 have roughly the same height; $W_1$ represents the width of the first path (i.e. the width of restriction 116 in trapping branch 113); $W_2$ represents the width of the second path (i.e. the width of bypass branch 114); $L_1$ (respectively $L_2$) represents the length of the first path (respectively of the second path); $\alpha_1$ (respectively $\alpha_2$) is the ratio between the width and height of the first path (respectively of the second path), satisfying the condition $\alpha_{1,2} \leq 1$; and $C_{1,2}(\alpha_{1,2})=f \times Re$, where f is a friction coefficient and Re is the Reynolds number. For satisfactory trapping, the value of P relative to the dimensions of fluid trapping circuit 112 is thus chosen such that it is greater than 1 whilst being minimised in order to limit encumbrance. It should be noted that P is independent of the flow rate intervals used subject to the states of laminary flow (Re<<1).

The diameter of the particle of interest is thus taken into account in determining the dimensioning of trapping circuit 112, and therefore of fluid system 11, which itself enables the dimensions of oscillator 7 to be determined. $W_1$ and $W_2$ are generally determined according to the dimension of the particle which it is desired to trap. After this, the other dimensional or fluid parameters of the device are determined, using equation (1).

For example, in order to retain particles of diameter 15 μm, the following parameters can be used for the channels of trapping circuit 112: a height H of 18 μm; a first path (restriction 116 in trapping branch 113) of width $W_1$ 7.5 μm and of length $L_1$ 4.5 μm; and a second path of width $W_2$ 20 μm and of length $L_2$ 172.5 μm. The ratio of the lengths of the first and second paths is thus 38.3 and the value of P is 3.95. It will be noted that 15 μm microbeads or particles can be functionalised in order to analyse hybridisation reactions or to undertake a specific detection of DNA, antigen or protein probes. Similarly, trapping site 21 can also be functionalised, increasing detection capacity.

According to a second example, if it is desired to retain smaller-sized particles or beads, for example of the order of 2 μm, and taking into account a manufacturing resolution of around 1 μm, the following parameters can be used to dimension trapping circuit 112: H=3 μm, $W_1$=1 μm, $W_2$=4 μm, which implies a lengths ratio of $$\frac{L_1}{L_2} > 24.7.$$

It is possible, for example, to take $$\frac{L_1}{L_2} = 50$$

and in this case the value of P is 2.03, which is sufficient for trapping site 21 to operate correctly, whilst remaining quite low in order to minimise encumbrance.

A third example which can be applied to cellular biology concerns the detection of HIV viruses which typically have a diameter of 100 nm and a mass of approximately 80 ag. In this case, the following parameters can be used to dimension the trapping circuit: H=200 nm, $W_1$=70 nm, $W_2$=150 nm, which implies a lengths ration $$\frac{L_1}{L_2}$$

at least equal to 7, and in the case of the lower limit, value P is 1.02.

Advantageously, fluid system 11 includes at least one trapping site 21 located at an antinode 23 of electromechanical oscillator 7. Placing trapping site at antinode 23 of oscillator 7 is advantageous, since it increases the sensitivity of detection of the particle of interest.

Indeed, when a particle of mass Δm becomes attached to electromechanical oscillator 7, the shift of resonant Δm frequency Δf of oscillator 7 depends on added mass Δm, the total mass m of oscillator 7, and on a correction coefficient α which depends specifically on the position of the added particle defined using the following equation:

$$\frac{\Delta f}{f} = -\alpha \frac{\Delta m}{m}$$

By trapping a particle of given point mass Δm in a position having maximum vibration amplitude, a maximum shift of resonant frequency is thus obtained. In other words, by trapping the particle in such a position (i.e. in an antinode), correction coefficient □ can be minimised, and consequently the sensitivity of the device can be increased.

As an example, FIG. 3 illustrates a map of the vibration amplitudes for an electromechanical oscillator 7 having the shape of a square plate. Capacitive excitation means 9 are used (via the electrodes), for example, to excite oscillator 7 with an excitation mode with a contour known as a Lame contour. Detection means 13 are also used to detect the oscillator's mechanical response in frequential terms.

The mechanical responses of oscillator 7 according to this example show that the corners and centre of the plate constitute vibration nodes 25 (zones of minimal vibration), whereas the middles of the sides of the plate constitute antinodes 23 (zones of maximum vibration amplitude).

The regionalisation of the mass response of oscillator 7 is thus used to place trapping site(s) 21 in zones 23 of maximum vibration amplitude according to its geometry and its excitation mode.

Advantageously, according to the present invention, the position of trapping site 21 within oscillator 7 allows an efficient linkage between the location with optimal mechanical response for mass detection of a particle, and a passive fluid trapping based on segregation by particle size.

Furthermore, vibration nodes 25 can be put to use to attach oscillator 7. Indeed, FIG. 3 shows that support means 27 in the form of arms are distributed at the corners of the square plate in order to minimise the mechanical stresses applied to the resonator during a vibrational cycle. The vibration is not then dissipated to the remainder of detection device 3, and is concentrated in oscillator 7. It will be noted that the arms are also used for passage of the connections between fluid system 11 and supply circuit 5.

It will be noted that the fluid system can include several trapping sites 21 located in the same vibration node 23 of oscillator 7.

In addition, if oscillator 7 includes several antinodes 23, fluid system 11 can include multiple trapping sites 21 located in the areas of the various antinodes 23 of oscillator 7.

Whatever the configuration, trapping sites 21 can be associated with the terminals of supply circuit 5 which are dependent on the sought application. Trapping sites 21 can thus be arranged in series, in parallel, or according to any other configuration combining both types of associations.

Figure 4A:
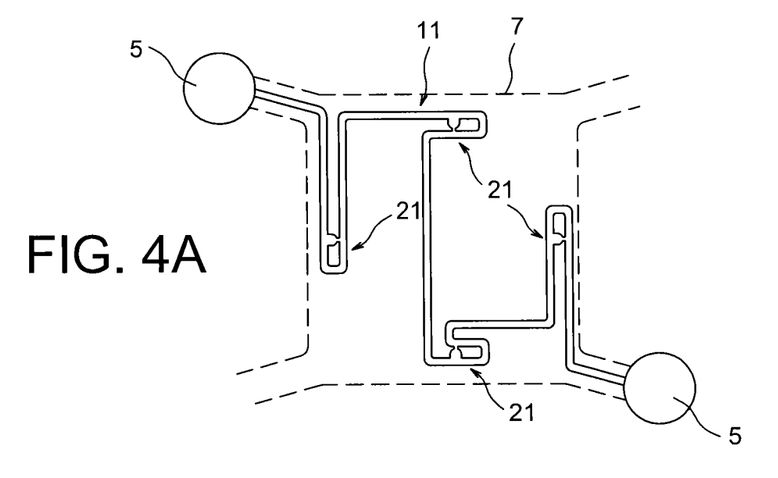
FIGS. 4A and 4B illustrate electromechanical oscillators of the hollow cavity plate type which is square in shape and incorporates fluid systems, according to the invention.
Figure 4B:
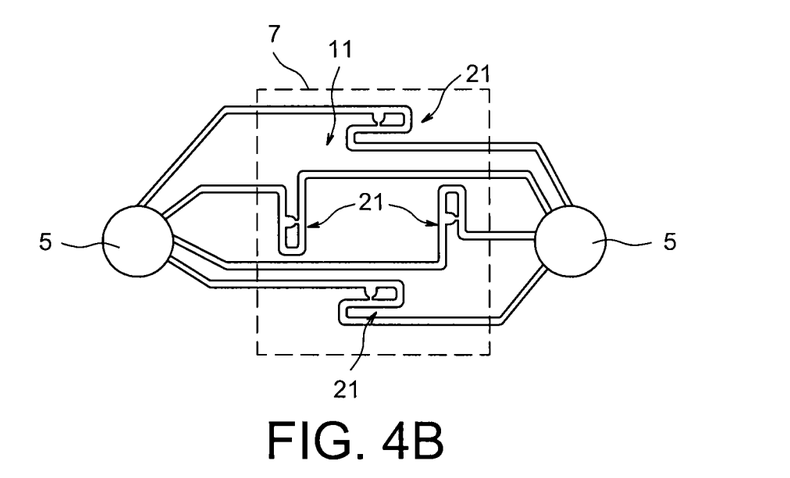

FIGS. 4A and 4B illustrate electromechanical oscillators of the hollow cavity plate type which is square in shape and incorporates fluid systems, in a series configuration (FIG. 4A) and parallel configuration (FIG. 4B).

The square-shaped oscillator is easy to manufacture and can be of a width and a thickness which are such that the ratio of the width to the thickness is greater than 10, and preferably between 10 and 30. This oscillator includes within it four trapping sites located at the four antinodes of the oscillator.

According to the example of FIG. 4A, trapping sites 21 are arranged in series at the terminals of supply circuit 5. Sites 21 are therefore occupied in a sequential manner.

Conversely, in the example of FIG. 4B, trapping sites 21 are arranged in parallel at the terminals of supply circuit 5, and each site 21 is directly connected to supply circuit 5. In this case, almost simultaneous trapping of the particles can be accomplished. In addition, trapping sites 21 can be dimensioned differently in order to trap particles of different sizes.

More generally, oscillator 7 of the hollow cavity plate type can take the shape of a disk, a ring or a polygon. The number of antinodes 23 naturally depends on the shape of the plate, but also on the vibration mode.

The oscillator can also take the form of a cantilever, a fixed-fixed beam, a nanowire, or a membrane which may possibly be pierced. In the case of a cantilever, which vibrates with the fundamental bending mode, there is only one antinode, at the free apex of the beam which vibrates with the greatest amplitude.

Furthermore, excitation means 9 can be chosen from among the following means: capacitive, piezo-electrical, piezo-metallic, electromagnetic, thermal, thermo-elastic, and optical.

Advantageously, the fluid trapping and the maximisation of the response of the mass detector according to the invention are independent of the excitation means, and therefore allow the most suitable vibrational excitation mode to be chosen. The vibrational mode may be chosen in accordance with the type of oscillator 7 and with the sought application. The vibrational mode can thus be one of the set constituted by an extensional vibrational mode, a Lame contour mode, a mode known as a wine-glass vibrational mode, a torsional vibrational mode, a bending vibrational mode and a membrane mode.

In addition, detection means 13 can also be chosen independently from among the following means: capacitive, piezo-electrical, piezo-metallic, piezo-resistive, thermo-elastic, and optical.

Figure 5:
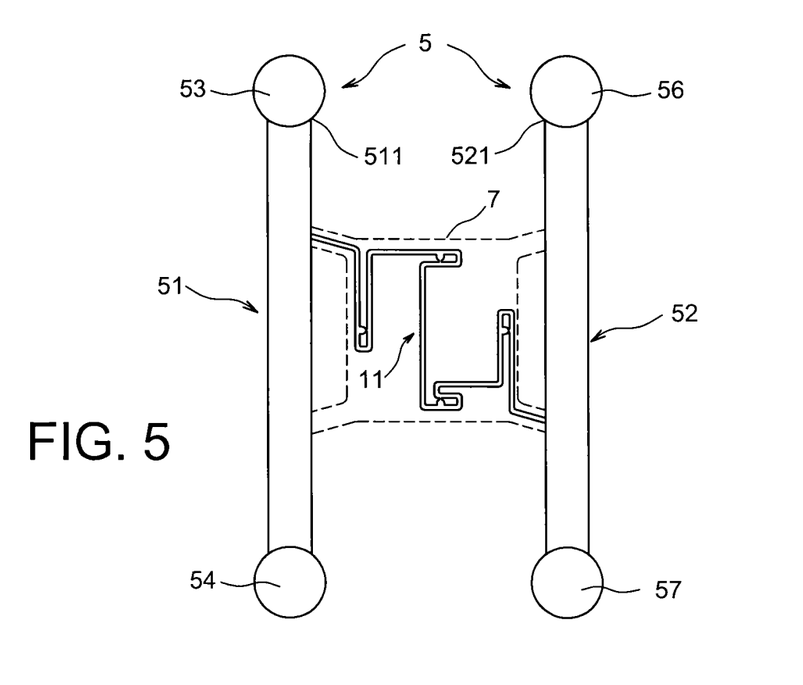
FIG. 5 illustrates the detection device in which the supply circuit includes supply channels according to a preferred embodiment of the invention.

FIG. 5 illustrates a detection device in which the supply circuit includes supply channels according to a preferred embodiment of the invention.

Supply circuit 5 includes first and second supply channels 51, 52 (or bypass channels), the sections of which are on a scale of a few hundreds of microns wide, and therefore much larger than those of the channels of fluid system 11, which are on a micrometric or nanometric scale. Upstream end 511 of first supply channel 51 is connected to a first fluid inlet 53 and its downstream end 513 is connected to a first fluid outlet 54. Similarly, upstream end 521 and downstream end 523 of second supply channel 52 are connected to second fluid inlet 56 and second fluid outlet 57 respectively. The inlet and outlets are interchangeable (in other words, an opening can be used as an inlet or an outlet, depending on how the device is to be used).

The first and second supply channels are separated from one another by the fluid system. Fluid system 11 is then a central system which is in communication firstly with first supply channel 51, and secondly with second supply channel 52, such that the flow rate in the fluid system can be controlled by adjusting the flow rates in the first and second supply channels. First and second supply channels 51, 52 are advantageously installed in a roughly symmetrical manner relative to central fluid system 11.

First and second supply channels 51, 52 enable the flow rate in central fluid system 11 to be adjusted accurately and simply. Indeed, it is possible to adjust the flow rate in each of supply channels 51, 52, and the flow rate differential between the two channels 51, 52 enables the flow rate to be controlled very finely in central fluid system 11.

In addition, first and second supply channels 51, 52, which have wide sections compared to central fluid system 11, can be rapidly drained, thus enabling the solutions of interest to be renewed easily. It is not therefore necessary to pass all the fluid through central system 11 (a pipe of small section implies a need to increase the pressure difference between upstream and downstream in order to maintain a high flow rate to drain), which would have taken much more time and where, in addition, there would have been risks of blockage or obstruction.

It will be noted that in the example of FIG. 5, trapping sites 21 are associated in series but, naturally, they can also be associated in parallel (see FIG. 4B) or according to any other configuration.

Figure 6A:
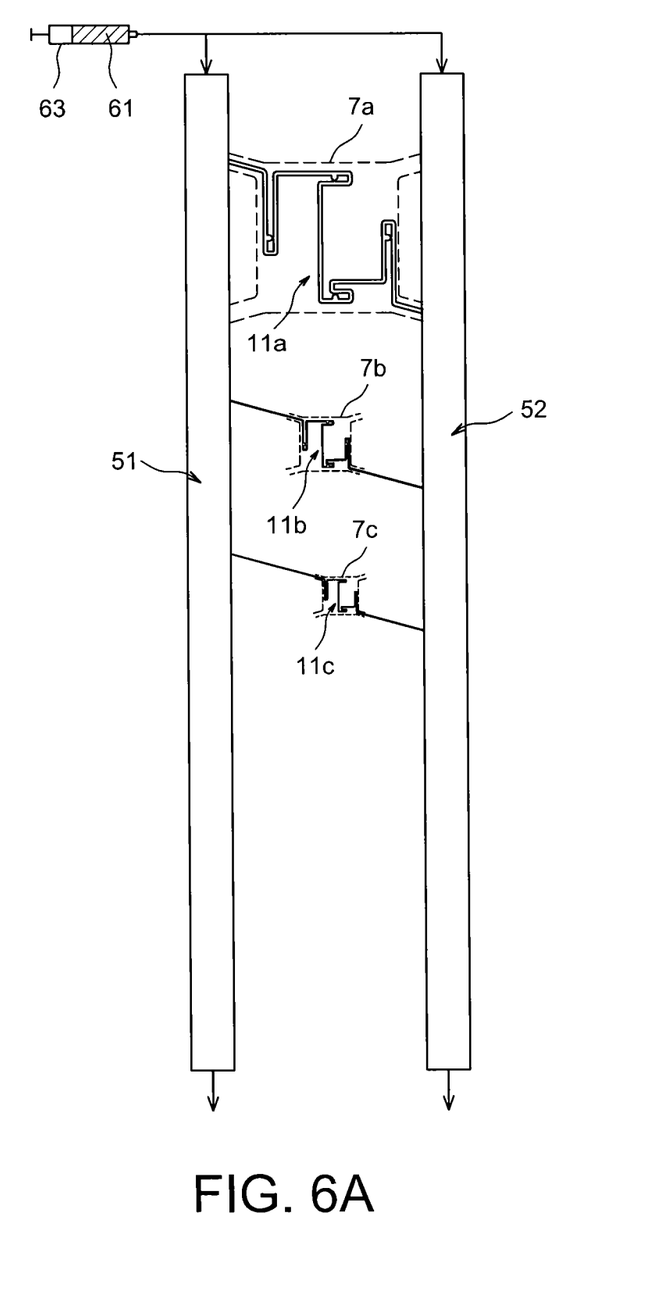
FIGS. 6A and 6B illustrate the detection device including a series of electromechanical oscillators of different scales according to preferred embodiments of the invention.

The fluid can also be supplied and directed by a flow generator of the syringe-driver type 63 (see FIG. 6). As a variant, the fluid can also be supplied and directed by a pressure generator (not represented) of the pressurised flask type.

Furthermore, it will be noted that it is also conceivable to have a supply circuit 5 including a single fluid inlet and a single fluid outlet, with the fluid system in direct communication between the fluid inlet and the fluid outlet (see FIGS. 4A, 4B).

Furthermore, the detection device according to the invention can also include an assembly of electromechanical oscillators 7 of identical or different scales, connected in series or in parallel with the terminals of supply circuit 5.

Figure 6B:
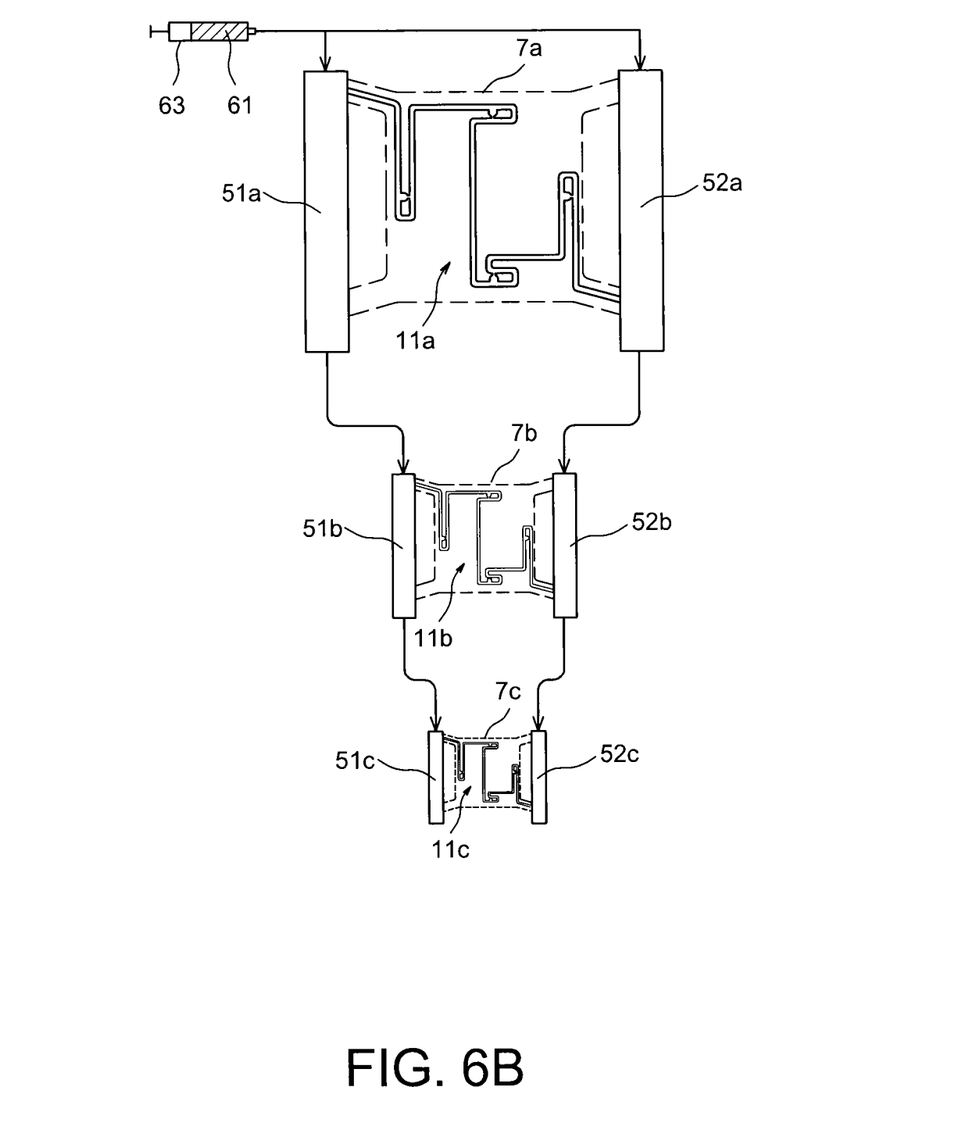

FIGS. 6A and 6B illustrate a detection device including a series of electromechanical oscillators of different scales according to preferred embodiments of the invention.

Each of electromechanical oscillators 7a-7c includes a fluid system 11a-11c of a corresponding scale, and the different fluid systems 11a-11c are in communication with first and second supply channels 51, 52.

Different fluid systems 11a-11c are connected in parallel between first and second supply channels 51, 52. A distribution of the liquid samples in a parallel configuration can thus traverse particle-trapping fluid systems 11a-11c starting with the largest size and ending with the smallest size (as represented in FIG. 6A) or conversely (not represented), by introducing a filtration module between the supply circuit and fluid systems 11a-11c.

The different fluid systems 11a-11c can thus selectively trap particles of variable sizes present in the fluid which is the solution of interest 61, supplied by supply generator 63. This is of particular interest for samples or solutions of interest of the serum type, which contain several species of particles of very different sizes. Thus, a first fluid system 11a can be dimensionally configured to trap cells of sizes 10 μm-100 μm, a second fluid system 11b can be dimensionally configured to trap bacteria of sizes 0.5 μm-5 μm, and a third fluid system 11c can be dimensionally configured to trap viruses of sizes 10 nm-400 nm.

The example of FIG. 6A shows that both first and second supply channels 51, 52 are of a constant section. Indeed, it is quite practical for manufacturing and drainage reasons to have supply channels of the same section along the entire length of the channels.

As a variant, FIG. 6B shows that both first and second supply channels 51, 52 can be formed from an assembly of segments 51a-51c, 52a-52c of different sections. This enables a given ratio of hydraulic resistances between supply segments 51a-51c, 52a-52c and those of central system 11a-11c to be maintained. It is thus possible to vary the order of magnitude of the hydraulic resistances of the supply channels in accordance with the scale of the fluid system, in order to better adjust the flow rates in the different systems 11a-11c.

According to another example, it is possible for each of the supply channels to have only two segments: a first segment connected to the microfluidic systems and a second segment of smaller section connected to the nanofluidic systems, enabling the flow rate range for the smallest fluid systems to be increased.

A method for mass detection of particles in a fluid medium according to the invention consists in implementing previously described detection device 3. This implementation includes the supply of fluid system(s) 11a-11c with a solution of interest 61 through supply channels 51, 52 such that target particles are trapped in the oscillator. Excitation means 9 are then used to cause oscillator(s) 7a-7c to vibrate at their respective resonant frequencies. Finally, detection means 13 are used to detect any shift of the resonant frequency relative to a reference frequency, indicating that a particle or particles has/have been trapped. A reference frequency is understood to mean, for example, a previously determined resonant frequency. This may notably be a resonant frequency before the fluid system is supplied with the solution of interest ("empty" resonator), or a resonant frequency during the supply of the system with the solution of interest, but measured at a prior instant.

Trapping signals or peaks can be observed in display means 17, indicating that the various trapping sites 21 are occupied.

Naturally, various modifications can be made by the skilled man in the art to the invention which has just been described, solely as non-restrictive examples.

The invention claimed is:

1. A device for mass detection of particles in a liquid medium, comprising:
   an electromechanical oscillator;
   excitation means fitted so as to cause said oscillator to vibrate at a frequency;
   a fluid supply circuit;
   a fluid system incorporated in said oscillator, said fluid system being in fluid communication with the fluid supply circuit and including at least one trapping site configured to trap a particle of interest according to the size of said particle of interest; and
   a detection means configured to detect a change in said frequency, said change being indicative of a mass of said particle of interest at said at least one trapping site,
   wherein said at least one trapping site is formed in a fluid trapping branch installed in parallel with a bypass fluid branch, where said trapping branch has, if the at least one trapping site is free, a lesser fluid resistance than that of said bypass branch,
   wherein said fluid trapping branch has an input end and an output end such that, if the at least one trapping site is free, a fluid flow upstream of the trapping branch is partially diverted through the input and output end of the trapping branch and the undiverted fluid flow flows through the bypass fluid branch and is rejoined with the diverted fluid flow at the output end of the trapping branch.

2. The detection device according to claim 1, wherein said at least one trapping site is located at at least one antinode of the electromechanical oscillator.

3. The detection device according to claim 2, wherein the fluid system includes multiple trapping sites located at different antinodes of said oscillator.

4. The detection device according to claim 3, wherein the trapping sites are arranged in series at terminals of the fluid supply circuit.

5. The detection device according to claim 3, wherein the trapping sites are arranged in parallel at terminals of the fluid supply circuit.

6. The detection device according to claim 1, wherein said oscillator is of a hollow cavity plate type, having a shape which may be chosen from among a disk, a ring, or a polygon.

7. The detection device according to claim 6, wherein said oscillator is square in shape and has a width and thickness such that a ratio of the width to the thickness is between 10 and 30.

8. The detection device according to claim 1, wherein said oscillator is a resonator of a cantilever, fixed-fixed beam, nanowire, or membrane type.

9. The detection device according to claim 1, wherein said excitation means is chosen from among the following means: capacitive, piezo-electrical, piezo-metallic, electromagnetic, thermal, thermo-elastic, and optical.

10. The detection device according to claim 1, wherein the detection means is selected from the group consisting of: capacitive, piezo-electrical, piezo-metallic, piezo-resistive, thermo-elastic, and optical devices.

11. The detection device according to claim 1, wherein said fluid system is a fluid microsystem or nanosystem.

12. The detection device according to claim 1, wherein the fluid supply circuit includes first and second supply channels, which are separated from one another by the fluid system, where said fluid system is in communication firstly with the first supply channel and secondly with the second supply channel, such that a flow rate in the fluid system may be controlled by adjusting flow rates in the first and second supply channels.

13. The detection device according to claim 12, further comprising an assembly of electromechanical oscillators of different scales, where each of the oscillators incorporates a fluid system of a corresponding scale, and in that the different fluid systems are in communication with the first and second supply channels.

14. A method for mass detection of particles in a liquid medium, implemented with a detection device including
   an electromechanical oscillator, a fluid supply circuit, a fluid system incorporated in said oscillator, said fluid system being in fluid communication with the fluid supply circuit, and at least one trapping site configured to trap a particle of interest according to the size of said particle of interest, and detection means configured to detect a change in a frequency of said oscillator, wherein said at least one trapping site is formed in a fluid trapping branch installed in parallel with a bypass fluid branch, where said trapping branch has, if the at least one trapping site is free, a lesser fluid resistance than that of said bypass branch, wherein said fluid trapping branch has an input end and an output end such that, if the at least one trapping site is free, a fluid flow upstream of the trapping branch is partially diverted through the input and output end of the trapping branch and the undiverted fluid flow flows through the bypass fluid branch and is rejoined with the diverted fluid flow at the output end of the trapping branch,
   the method comprising:
   supplying the fluid system with a solution of interest
   causing the oscillator to vibrate at a resonant frequency, and
   detecting a shift of the resonant frequency relative to a reference resonant frequency, said shift being indicative of a mass of said particle of interest at said at least one trapping site.

* * * * *